US007642280B2

(12) United States Patent
Fahey et al.

(10) Patent No.: US 7,642,280 B2
(45) Date of Patent: Jan. 5, 2010

(54) INHIBITORS OF ACYL GLUCOSAMINYL INOSITOL AMIDASE AND METHODS OF USE

(75) Inventors: Robert C. Fahey, Del Mar, CA (US); Gerald L. Newton, San Diego, CA (US); Carole A. Bewley, Bethesda, MD (US); Gillian Nicholas, Boulder, CO (US)

(73) Assignees: The Regents of the University of California, Oakland, CA (US); National Institutes of Health, Bethesda, MD (US)

( * ) Notice: Subject to any disclaimer, the term of this patent is extended or adjusted under 35 U.S.C. 154(b) by 362 days.

(21) Appl. No.: 10/474,138

(22) PCT Filed: Apr. 8, 2002

(86) PCT No.: PCT/US02/11117

§ 371 (c)(1),
(2), (4) Date: Mar. 15, 2004

(87) PCT Pub. No.: WO02/081483

PCT Pub. Date: Oct. 17, 2002

(65) Prior Publication Data

US 2004/0167331 A1 Aug. 26, 2004

Related U.S. Application Data

(60) Provisional application No. 60/282,096, filed on Apr. 6, 2001.

(51) Int. Cl.
A61K 31/415 (2006.01)
A61K 31/15 (2006.01)
C07D 223/00 (2006.01)
C07C 259/00 (2006.01)

(52) U.S. Cl. .................... 514/398; 514/640; 548/331.5; 564/253

(58) Field of Classification Search .................. 564/253; 514/398, 640; 548/331.5
See application file for complete search history.

(56) References Cited

OTHER PUBLICATIONS

Kobayashi et al. "Purealidins J—R, New Bromotyrosine Alkaloids from the Okinawan Marine Sponge Psammaplysilla purea" Chem. Pharm. Bull. 1995, vol. 43, Iss 3, pp. 403-407.*

Le Pecq et al. "A New Antitumoral Agent: 9-Hydroxyellipticene. Possibility of a Rational Design of Anticancerous Drugs in the Series of DNA Intercalating Drugs" PNAS, 1974, vol. 71, No. 12, pp. 5078-5082.*
Benharref, A. and Pais, M., "Bromotyrosine Alkaloids from the Sponge *Pseudoceratina verrucosa,*", *J. Nat. Prod.*, vol. 59, pp. 177-180, (1996).
Bewley et al., "Aciculitins A-C: Cytotoxic and Antifungal Cyclic Peptides from the Lithistid Sponge *Acicultes orientalis*", *J. Am. Chem. Soc.*, 118:4314-4321, (1996).
Davis-Coleman, M.T. et al, "A New EGF-Active Polymeric Pyridinium Alkaloid from the Sponge *Callyspongia fibrosa*", *J. Org. Chem.*, vol. 58:5925-5930 (1993).
Litaudon, M. et al, "Ianthelline, Un Nouveau Derive de la Dibromo-3,5 Tyrosine, Isole de L'eponge *Inathella ardis* (Bahamas)", *Tetrahedron Lett.*, 27:4455-4456 (1986).
Newton, G.L et al, "Distribution of Thiols in Microorganisms: Mycothiol Is a Major Thiol in Most Actinomycetes", *J. Bacteriol*, vol. 178(7):1990-1996. (1996).
Newton, G.L et al, "*N*-Acetyl-1-D-Myo-Inosityl-2-Amino-2Deoxy-α-D-Glucopyranoside Deacetylase (MshB) is a Key Enzyme in Mycothiol Biosynthesis", *J. Bacteriol*, 182(24):6958-6963 (2000).
Newton, G.L et al, "The Structure of U17 Isolated from *Streptomyces clavuligerus* and its Properties as An Antioxidant Thiol", *Eur. J. Biochem*, 230:821-825 (1995).
Newton, G.L., et al., "A Novel Mycothiol-Dependent Detoxification Pathway in Mycobacteria Involving Mycothiol S-Conjugate Amidase", *Biochemistry* 39(35):10739-10746 (2000).
Nicholas, G.M. et al, "Oceanapiside, an Antifungal Bis-α,ω-amino Alcohol Glycoside from the Marine Sponge *Oceanapia phillipensis*", *J. Nat. Prod.*, vol. 62:1678, (1999).
Nicholas, G.M. et al, "Novel Bromotyrosine Alkaloids: Inhibitors of Mycothiol S-Conjugate Amidase", *Organic Lett.*, vol. 3(10):1543-1545, (2001).
Sharma, et al., "New 9β-Lanostane-Type Triterpenic and 13,14-seco-Steriodal Esters from the Roots of *Artemisia scoparia*", *J. Nat. Prod.* 59:181-184 (1996).

* cited by examiner

*Primary Examiner*—Rei-Tsang Shiao
*Assistant Examiner*—Joseph R Kosack
(74) *Attorney, Agent, or Firm*—DLA Piper LLP (US)

(57) ABSTRACT

The present invention provides compounds with activity as inhibitors of acyl glucosaminylinositol amidases with amidase activity against S-conjugate amides, particularly mycothiol-derived S-conjugate amides. Certain of the invention compounds are naturally occurring compounds obtained from marine sponges and other organisms. The invention further provides methods for using the compounds to inhibit virulence and reduce antibiotic resistance of mycothiol-producing bacteria.

3 Claims, 7 Drawing Sheets

Mycothiol, MSH, AcCys-GlcN-Ins,
1-D-*myo*-inosityl-2-(*N*-acetyl-L-cysteinyl)-
amido-2-deoxy-α-D-glucopyranoside ADDITIONAL DATA ON INHIBITORS OF MYCOTHIOL S-CONJUGATE
AMIDASE ACTIVITY WITH 50 μM MSmB AS SUBSTRATE

| COMPOUND | IC$_{50}$ | STRUCTURE |
|---|---|---|
| C2385-2-2 | > 1 mM | 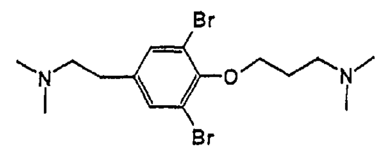 |
| Oceanapiside | 5 μM | 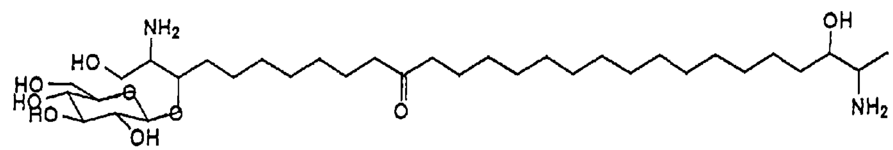 |
| 3-alkylpyridinium macrocycles n = 3-6 | ~50 ng/ml | 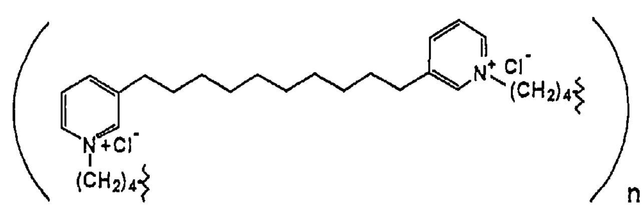 |

FIGURE 6

INHIBITORS OF ACYL GLUCOSAMINYL INOSITOL AMIDASE AND METHODS OF USE

RELATED APPLICATIONS

This application claims benefit of priority as a 371 filing of PCT/US02/11117, filed Apr. 8, 2002 which claims benefit of priority to U.S. Provisional Application No. 60/282,096, filed Apr. 6, 2001, both of which are herein incorporated by reference in their entirety.

GRANT INFORMATION

This invention was made with government support under Grant No. AA011391 awarded by National Institutes of Health. The government has certain rights in the invention.

FIELD OF THE INVENTION

The present invention generally relates to antibacterial compounds and their use, and more specifically to inhibitors of acyl glucosaminyl inositol amidase activity and methods of their use in treatment of bacterial infection.

BACKGROUND OF THE INVENTION

Mycothiol (MSH) is a low molecular weight thiol that replaces glutathione in actinomycetes (G. L. Newton et al. *J. Bacteriol.* (1996) 178:1990). In conjunction with MCA, MSH plays a central role in protecting actinomycetes against alkylating agents and other toxins (G. L. Newton, et al. *Biochemistry* (2000a) 39:10739). Recently a second highly homologous amidase from *M. tuberculosis* that is involved in the biosynthesis of MSH has been described (G. L. Newton et al. *J. Bacteriol.* (2000) 24:6958).

Aerobic organisms are subjected to oxidative stress from many sources, including atmospheric oxygen, basal metabolic activities, and, in the case of pathogenic microorganisms, toxic oxidants from the host phagocytic response intended to destroy the bacterial invader. Glutathione (GSH) is the dominant low molecular weight thiol in most eukaryotes and Gram-negative bacteria, and it plays a key role in protection of the cell against oxygen toxicity and electrophilic toxins (R. C. Fahey and A. R. Sundquist (1991) *Adv. Enzymol.* 64:1-53; Dolphin, et al, (1989) *Glutathione: Chemical, Biochemical, and Medical Aspects* pp 45-84, John Wiley & Sons, New York). However, actinomycetes, including *Streptomyces* and *Mycobacteria* do not make GSH but produce millimolar levels of mycothiol (MSH, AcCys-GlcN-Ins), an unusual conjugate of N-acetylcysteine (AcCys) with 1-D-myo-inosityl-2-amino-2-deoxy-α-D-glucopyranoside (GlcN-Ins) (G. L. Newton, et al. (1996) *J. Bacteriol.* 178: 1990-1995; S. Sakuda, et al., (1994) Biosci. Biotech. Biochem. 58:1347-1348; H. S. C. Spies and D. J. Steenkamp, (1994) *Eur. J. Biochem.* 224:203-213; G. L. Newton, et al. (1995) *Eur. J. Biochem.* 230:821-825) (FIG. 1A).

Antibiotic resistance of pathogenic bacteria, including pathogenic actinomycetes, such as *M. tuberculosis*, is a well-known problem faced by medical practitioners in treatment of bacterial diseases. *Mycobacterium tuberculosis*, the causative agent of tuberculosis, is a leading pathogenic cause of death worldwide (Zumla, A. et al. *Clinical Review: Tuberculosis. Br. Med. J.* (1998) 316:1962). The rise of mycobacterial resistance to common antituberculars such as isoniazid and rifampin, along with the high prevalence of tuberculosis and Mycobacterium avium complex in AIDS patients, has led to a renewed interest in the discovery of antimycobacterial agents with new modes of action.

Therefore, there is a further need in the art for a new class of compounds useful for reducing resistance to existing antibiotics in treatment of bacterial infections in humans and in other mammals, such as domestic and farm animals and useful as antibiotics in treatment of bacterial diseases such as tuberculosis.

SUMMARY OF THE INVENTION

The present invention overcomes these and other problems in the art by providing compounds that are useful for their ability to inhibit a mycobacterial acyl glucosaminyl inositol amidases, such as, mycothiol S-conjugate amidase (MCA). In one embodiment, the invention inhibitors of acyl glucosaminyl inositol amidase have the chemical structure of Structure I or Structure II:

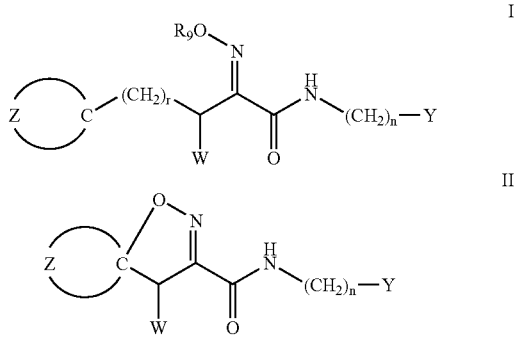

wherein Z together with the carbon to which it is attached is a monocyclic, bicyclic, tricyclic, tetracyclic or pentacyclic ring, each containing 5-7 members, wherein 0-2 of the members are independently selected from oxygen, sulfur and nitrogen and the remaining members are carbon, wherein each ring contains 0-3 double bonds and is substituted with up to 4 substituents $X_1$, $X_2$, $X_3$ or $X_4$;

wherein $X_1$, $X_2$, $X_3$ and $X_4$ are independently selected from —F, —Cl, —Br, —I, —OH, —OCH$_3$, and —O(CH$_2$)$_m$Q, wherein m=any integer from 1 to 4 and wherein Q is selected from —NH$_2$, —NH(CH$_2$)$_s$CH$_3$, —N[(CH$_2$)$_s$CH$_3$]$_2$, —N$^+$[(CH$_2$)$_s$CH$_3$]$_3$, wherein s=0 or any integer from 1 to 3, n=any integer from 1 to 6, and r=0 or any integer from 1 to 4;

Y is either selected from N-substituted 2-aminoimidazole and:

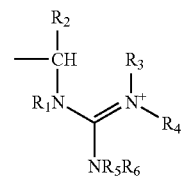

wherein $R_1$, $R_2$, $R_3$, $R_4$, $R_5$, and $R_6$ are independently selected from —H, —CH$_3$, and —(CH$_2$)$_p$CH$_3$, wherein p=0 or any integer from 1 to 3, except that —CHR$_2$ and R$_3$ can join to become —C=CR$_7$, forming an imidazole ring, and then R$_7$ is selected from: H,

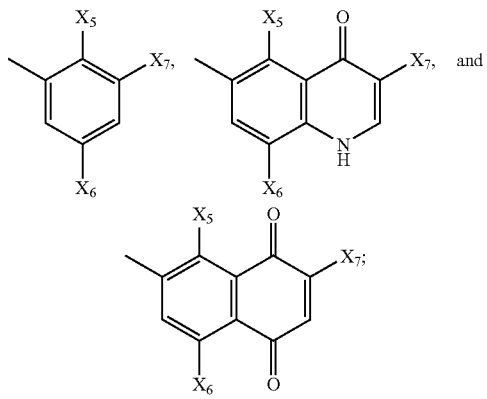

wherein $X_5$, $X_6$, and $X_7$ are independently selected from —H, —F, —Cl, —Br, —I, —OH, —OCH$_3$, —NH$_2$, —CONH$_2$ and —O(CH$_2$)$_m$Q, wherein m=any interger form 1 to 4 and wherein Q is selected from —NH$_2$, —NH(CH$_2$)$_r$CH$_3$, —N[(CH$_2$)$_s$CH$_3$]$_2$, —N$^+$[(CH$_2$)$_s$CH$_3$]$_3$, wherein s=0 or any integer from 1 to 3, n=any integer from 1 to 6, and r=0 or any integer from 1 to 4;

or Y is —O—R$_8$, wherein R$_8$ is

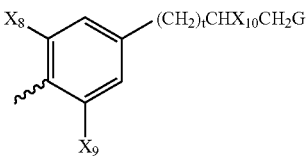

wherein $X_8$ and $X_9$ are independently selected from —F, —Cl, —Br, —I, —OH, —OCH$_3$, and —O(CH$_2$)$_m$Q, wherein m=any integer from 1 to 4 and wherein Q is selected from —NH$_2$, —NH(CH$_2$)$_s$CH$_3$, —N[(CH$_2$)$_s$CH$_3$]$_2$, —N$^+$[(CH$_2$)$_s$CH$_3$]$_3$, wherein s=0 or any integer from 1 to 3, n=any integer from 1 to 6, and r=0 or any integer from 1 to 4;

wherein $X_{10}$ is selected from —H or —OH, G is selected from —H, —NH$_2$, —N$^+$[(CH$_2$)$_s$CH$_3$]$_3$, —NHC(NH$_2$)=NH, or 2-aminoimidazole, wherein s=0-3, and R$_9$ is selected from —H, CH$_3$, (CH$_2$)$_s$CH$_3$ wherein s=0, or any integer from 1 to 3.

In another embodiment the invention inhibitors of acyl glucosaminyl inositol amidase have the chemical structure

III

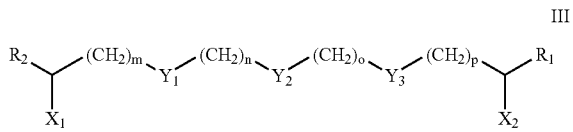

wherein m=any integer from 1 to 6, n=any integer from 1 to 6, o=any integer from 1 to 6, p=any integer from 1 to 6; $Y_1$, $Y_2$, and $Y_3$ are independently selected from —CH$_2$—, —O—, —S—, —CO—, and —CH(CONHOH)—, $X_1$ and $X_2$ are independently —H or —OR, wherein R=—H, glucose, glucosamine, acetylglucosamine, glucosaminyl inositol; $R_1$ and $R_2$ are either independently selected from the group consisting of:

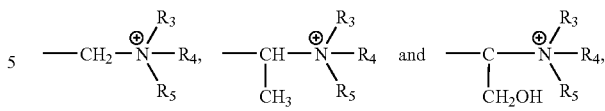

wherein $R_3$, $R_4$ and $R_5$ are optionally present and when present are independently selected from —H and —(CH$_2$)$_m$CH$_3$, wherein m=0, or any integer from 1 to 3;

or $R_1$ and $R_2$ are independently selected from the group consisting of:

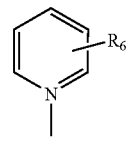

wherein $R_6$ is (CH$_2$)$_q$OCH$_3$ or (CH$_2$)$_q$CH$_3$, wherein q=any integer from 1 to 11,

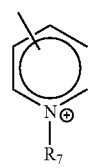

wherein $R_7$ is (CH$_2$)$_q$OCH$_3$ or (CH$_2$)$_q$CH$_3$, wherein q=any integer from 1 to 11,

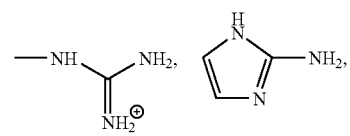

and pharmaceutically suitable salts thereof

In yet another embodiment according to the present invention, there are provided methods for decreasing the antibiotic-resistance of pathogenic acyl glucosaminyl inositol amidase-producing bacteria by introducing into the bacteria an invention inhibitor of acyl glucosaminyl inositol amidase activity. The intracellular presence of the inhibitor decreases activity of the amidase, thereby decreasing the mycothiol content and decreasing the antibiotic-resistance of the bacteria as compared with untreated control bacteria.

In still another embodiment according to the present invention, there are provided methods for reducing the virulence in a subject of pathogenic acyl glucosaminyl inositol amidase-producing bacteria by administering to the subject an effective amount of an invention inhibitor, wherein the inhibitor has inhibitory activity against acyl glucosaminyl inositol amidase for acyl glucosaminyl inositol amides, wherein administration of the inhibitor to the subject reduces the growth rate of the bacteria in the subject, thereby reducing the virulence of the bacteria in the subject as compared to an untreated subject.

BRIEF DESCRIPTION OF THE FIGURES

FIG. 6 shows the chemical structures of three compounds screened for activity as inhibitors of acyl glucosaminyl inositol amidase and the $IC_{50}$s of these compounds as determined by the method of Example 2.

DETAILED DESCRIPTION OF THE INVENTION

Figure 1A:
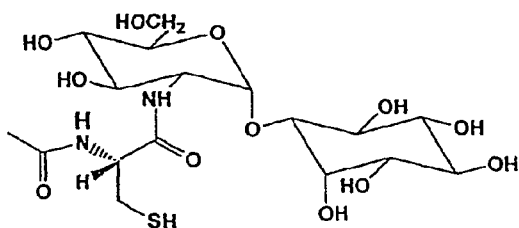
FIG. 1A is a drawing showing the chemical structure of mycothiol (AcCys-GlcN-Ins) (MSH), chemical name 1-D-myo-inosityl-2-(N-acetylcysteinyl)amido-2-deoxy-α-D-glucopyranoside.

In accordance with the present invention, there are provided compounds with inhibitory activity against an acyl glucosaminyl inositol amidase, which amidase is produced naturally in mycobacteria and has enzymatic amidase activity for a glucosaminyl inositol (GlcN-Ins)-containing substrate.

In one embodiment, the invention inhibitors of acyl glucosaminyl inositol amidase have the chemical structure of Structure I or Structure II:

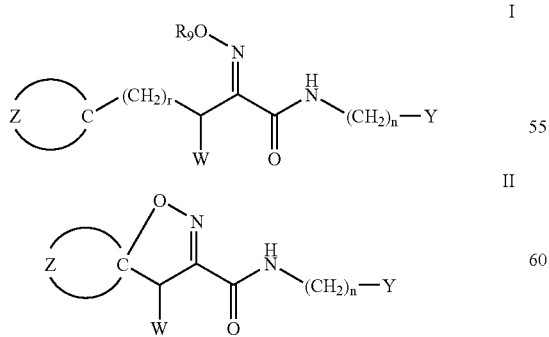

wherein Z together with the carbon to which it is attached is a monocyclic, bicyclic, tricyclic, tetracyclic or pentacyclic ring, each containing 5-7 members, wherein 0-2 of the members are independently selected from oxygen, sulfur and nitrogen and the remaining members are carbon, wherein each ring contains 0-3 double bonds and is substituted with up to 4 substituents $X_1$, $X_2$, $X_3$ or $X_4$;

$X_1$, $X_2$, $X_3$ and $X_4$ are independently selected from —F, —Cl, —Br, —I, —OH, —$OCH_3$, and —$O(CH_2)_mQ$, wherein m=any integer from 1 to 4 and wherein Q is selected from —$NH_2$, —$NH(CH_2)_sCH_3$, —$N[(CH_2)_sCH_3]_2$, —$N^+[(CH_2)_sCH_3]_3$, wherein s=0, or any integer from 1 to 3, n=any integer from 2 to 6, and r=0, or any integer from 1 to 4;

Y can either have the structure:

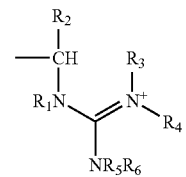

wherein $R_1$, $R_2$, $R_3$, $R_4$, $R_5$, and $R_6$ are independently selected from —H, —$CH_3$, and —$(CH_2)_pCH_3$, wherein p, 0, or any integer from 1 to 3, except that $R_4$ is optionally present and except that —$CHR_2$ and $R_3$ can join to become —C═$CR_7$, forming an imidazole ring, and then $R_7$ is selected from: H,

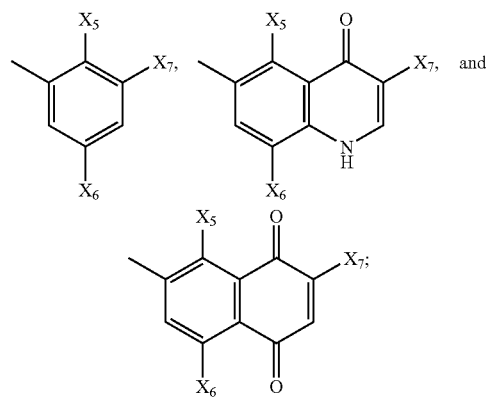

wherein $X_5$, $X_6$, and $X_7$ are independently selected from —H, —F, —Cl, —Br, —I, —OH, —$OCH_3$, —$NH_2$, —$CONH_2$ and —$O(CH_2)_mQ$, wherein m=1-4 and wherein Q is selected from —$NH_2$, —$NH(CH_2)_sCH_3$, —$N(CH_2)_sCH_3$, and —$N^+(CH_2)_sCH_3$, wherein s=0, or any integer from 1 to 3;

or Y can be —O—$R_8$, wherein $R_8$ is

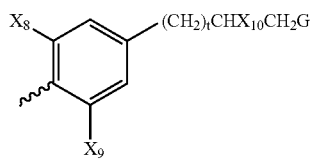

wherein $X_8$ and $X_9$ are independently selected from —F, —Cl, —Br, —I, —OH, —$OCH_3$, and —$O(CH_2)_mQ$, wherein m=1-4 and wherein Q is selected from —$NH_2$, —$NH(CH_2)_sCH_3$, —$N(CH_2)_sCH_3$, and —$N^+(CH_2)_sCH_3$, wherein s=0, or any integer from 1 to 3, t=0, or any integer from 1 to 4.

$X_{10}$ is selected from —H or —OH, and G is selected from —H, —$NH_2$, —$N^+[(CH_2)_sCH_3]_3$, —$NHC(NH_2)$=NH, and 2-aminoimidazole, wherein s=0, or any integer from 1 to 3, and $R_9$ is selected from —H, $CH_3$, $(CH_2)_sCH_3$ wherein s=0, or any integer from 1 to 3.

For example, the invention inhibitors can have a chemical structure as described by Structure I above, wherein Z is a substituted or unsubstituted bromotyrosine, or as described by Structure II wherein Z is a substituted or unsubstituted bromotyrosine-derived spiro-isoxazoline, wherein n=1 or 2. In another example the compound can have Structure II wherein Y is

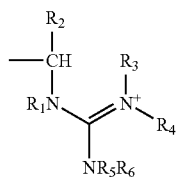

or the Structure II wherein Y is

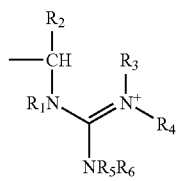

except that —$CHR_2$ and $R_3$ join to form the imidazole ring, wherein $R_7$ is —H.

Alternatively, the invention inhibitor can have Structure II, wherein Z is a 7-membered ring containing one oxygen member, W=—OH and n=1 or 2, including such compounds wherein Y is —O—$R_8$, for example one wherein Y is —O—$R_8$, $X_8$ and $X_9$ are each —Br, $X_{10}$ is —OH, n=2, t=0, and G is —$NH_2$.

In another alternative, the invention inhibitor can have a chemical structure described by Structure I above, wherein Z is a 6-membered ring, $X_1$ and $X_3$ are each —Br, $X_2$ is —$O(CH_2)_mQ$, m=3, Q is —$NH_2$, and n=1 or 2, including such compounds wherein Y is

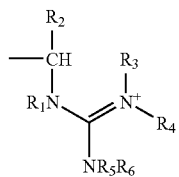

except that —$CHR_2$ and $R_3$ join to form the imidazole ring, and $R_7$ is —H and compounds wherein Y is

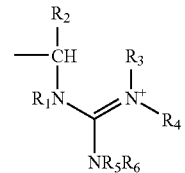

except that $R_4$ is not present and the positive charge on the nitrogen is not present.

A presently preferred example of the invention inhibitors has the chemical structure:

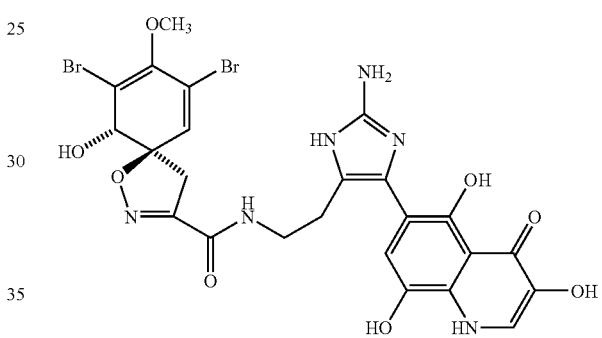

Another invention inhibitor that is presently preferred has the chemical structure:

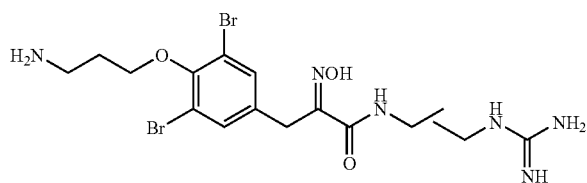

In another embodiment the invention inhibitors of acyl glucosaminyl inositol amidase have the following chemical structure:

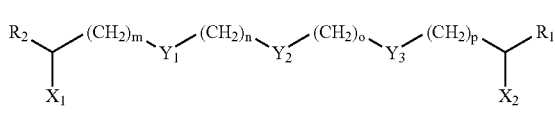

III wherein m=any integer from 1 to 6, n=any integer from 1 to 6, o=any integer from 1 to 6, p=any integer from 1 to 6; $Y_1$, $Y_2$, and $Y_3$ are independently selected from —$CH_2$—, —O—, —S—, —CO—, and —CH(CONHOH)—, $X_1$ and $X_2$ are independently —H or —OR, wherein R=—H, glucose, glucosamine, acetylglucosarnine, glucosaminyl inositol; and $R_1$ and $R_2$ are either independently selected from the group consisting of:

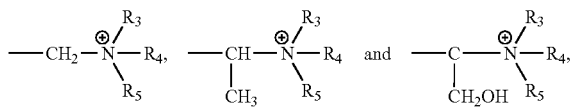

wherein $R_3$, $R_4$ and $R_5$ are optionally present and when present are independently selected from —H and —$(CH_2)_mCH_3$, wherein m=0, or any integer from 1 to 3;

or $R_1$ and $R_2$ are independently selected from the group consisting of:

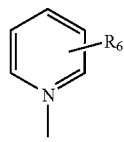

wherein $R_6$ is $(CH_2)_qOCH_3$ or $(CH_2)_qCH_3$, wherein q=any integer from 1 to 11,

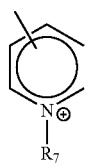

wherein $R_7$ is $(CH_2)_qOCH_3$ or $(CH_2)_qCH_3$, wherein q=any integer from 1 to 11,

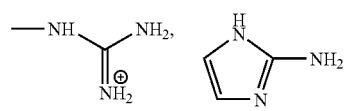

and pharmaceutically suitable salts thereof.

For example, the invention inhibitors can be exemplified in the compound having Structure III wherein $Y_1$=—$CH_2$—, $Y_2$=—CO—, $Y_3$=—$CH_2$—, m=4, n=4, o=6, and p=5.

Alternatively, the invention inhibitor can have Structure III wherein $X_1$ is —OR, R=glucose, $X_2$ is —OR, R=H, $R_2$ is

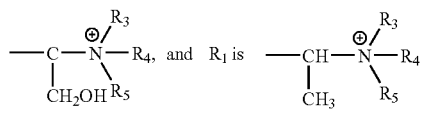

In yet another example, the invention inhibitor can have a chemical structure exemplified by Structure III, wherein $X_1$ is —OR, R=H, $X_2$ is —OR, R=H, $R_2$ is

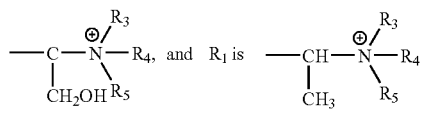

Alternatively, the invention inhibitor can have a chemical structure exemplified by Structure III, wherein $Y_1$, $Y_2$ and $Y_3$ are —$CH_2$—, m=n=1, o=any integer from 1 to 4, and p=any integer from 1 to 4, $R_2$ is

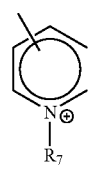

wherein $R_7$ is $(CH_2)_qOCH_3$ or $(CH_2)_qCH_3$, wherein q=any integer from 1 to 11, and $R_1$ is

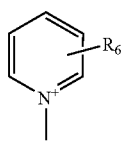

wherein $R_6$ is $(CH_2)_qOCH_3$ or $(CH_2)_qCH_3$, wherein q=any integer from 1 to 11.

Particular examples of the invention inhibitors having Structure III that are presently preferred are compounds having the following chemical structures:

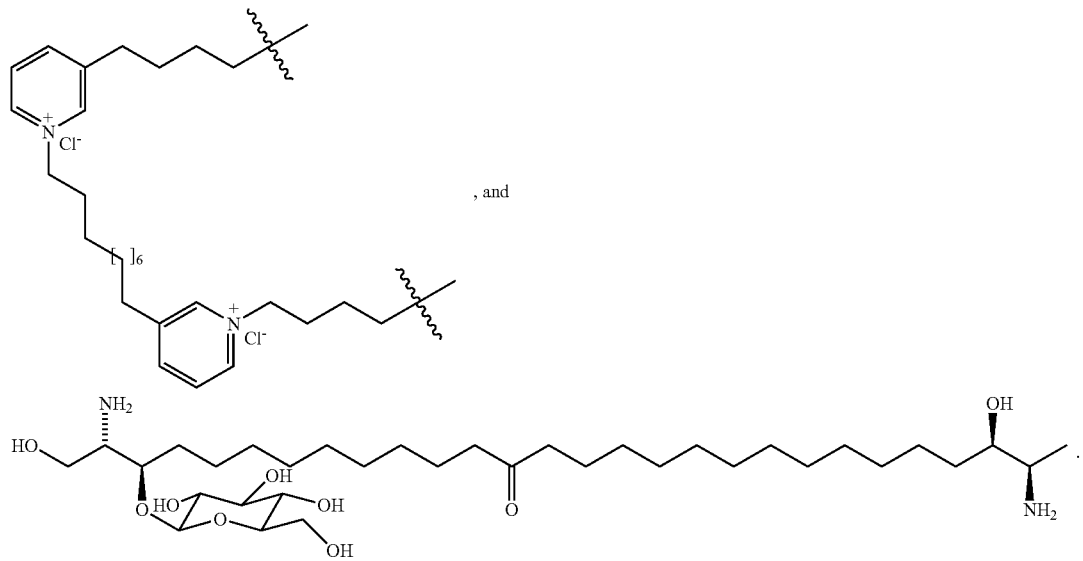

The invention inhibitors are chemical compounds that act to inhibit enzymatic activity of an of acyl glucosaminyl inositol amidase. Thus, the invention inhibitors have antimycobacterial activity, especially against an *actinomycetes*, such as *M. smegmatis* or *M. tuberculosis*. The invention compounds also inhibit growth of antibiotic-producing bacteria. The invention inhibitors can be purified from natural organisms using techniques known in the art and as described herein. In addition, the invention inhibitors can be chemically synthesized using techniques well known in the art.

As used herein the term "acyl glucosaminyl inositol amidase" refers to polypeptides with enzymatic amidase activity for glucosaminyl inositol (GlcN-Ins)-containing substrates.

As used herein, the term "acyl glucosaminyl inositol amidase" means an amidase that hydrolyzes a substrate having the chemical formula R—CONH-GlcN-Ins wherein R=$CH_3$($CH_2$)$_n$— where n=0-6. Included in the group of substrate compounds is the natural substrate, acetyl-GlcN-Ins, where n=0. Members of this group of substrate compounds are derived from an alkanoic acid. In addition, compounds having the chemical structure R—CONH-GlcN-Ins wherein R=aryl-($CH_2$)$_n$, where n=0-6 are encompassed by the term. Members of this group of substrate compounds are derived from an aryl alkanoic acid such as phenyl-($CH_2$)$_n$COOH.

The acyl glucosaminyl inositols of the above chemical formula can also be derived from the reaction of GlcN-Ins with any commercial acid chloride in the form RCOCl, wherein R is: o-tolyl-, 4-ethylphenyl-, 4-propylphenyl-, 4-biphenyl-, 3,4-dimethoxyphenyl-, 3,4,5-trimethoxyphenyl-, 2-furyl-, and the like.

The acyl glucosaminyl inositols of the above chemical formula can also be derived from an amino acid or an N-acetyl amino acid. Preferred amino acids include N-acetylcysteinyl-S—R' or cysteinyl-S—R', wherein R' is an organic group attached to the cysteine sulfur, such as may be derived from commercial thiol labeling reagents like 2-bromoacetophenone, monobromobimane, N-ethylmaleimide, 7-diethylamino-3-(4'-maleimidyl phenyl)-4-methyl coumarin, 3(N-maleimidopropionyl)biocytin, and from naturally occurring antibiotics, including cerulenin, granaticin A, naphthomycin A, naphthomycin H, and the like.

Figure 1B:
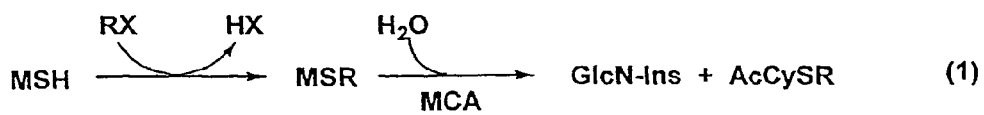
FIG. 1B is a schematic representation of the reaction wherein MSH is alkylated (R=alkylating group) to MSR and broken down by enzyme mycothiol S-conjugate amidase (MCA) to form 1-D-myo-inosityl-2-amino-2-deoxy-α-D-glucopyranoside (GlcN-Ins) and a mercapturic acid (Ac-CysR).

A subset of the acyl glucosaminyl inositol amidases that are inhibited by the invention inhibitors are referred to herein as mycothiol S-conjugate amidases, whose substrate is an S-conjugate of a cysteine amide. As used herein, the term "S-conjugate" means that the molecule is a thioether or thioester containing two chemical moieties joined by a sulfur (i.e., —S—) moiety. In a preferred embodiment the S-conjugate molecule is derived from mycothiol (FIG. 1A) by the reaction shown in FIG. 1B, wherein RX is an electrophile and R is an alkyl or alkyloid moiety. However, inhibitors of acyl glucosaminyl inositol amidases of the invention do not require a sulfur-containing amide substrate and instead cleave an GlcN-Ins-containing amide substrate.

As used herein, the terms "GlcN-Ins-containing amide" and "glucosaminyl inositol-containing amide" are interchangeable when used to describe a substrate molecule for which an acyl glucosaminyl inositol amidase has enzymatic activity, resulting in cleavage of the molecule. Similarly, the term "amide-containing S-conjugate" and "S-conjugate-containing amide" are interchangeable when used to describe a substrate molecule for which an S-conjugate amidase has enzymatic activity, resulting in cleavage of the molecule. If a particular amidase is an amide hydrolase, cleavage of the substrate molecule will form breakdown products wherein one product is a carboxylic acid, (e.g., a carboxylic acid containing at least one sulfur moiety) and the other product is a amine (e.g., GlcN-Ins). If the substrate is a mycothiol-derived S-conjugate amide of the type illustrated in FIG. 1B, one of the breakdown products will be 1-D-myo-inosityl-2-amino-2-deoxy-α-D-glucopyranoside (GlcN-Ins) and the other breakdown product will be a sulfur-containing carboxylic acid, such as a mercapturic acid. AcCys S-conjugates are termed mercapturic acids, the final excreted product in the mercapturic acid pathway of glutathione-dependent detoxification in mammals (J. L. Stevens, et al., (1989) in *Glutathione: Chemical, Biochemical, and Medical Aspects— Part B* (D. Dolphin, et al.) pp 45-84, John Wiley & Sons, et al.).

It is known that acyl glucosaminyl inositol amidases participate in a pathway of detoxification in bacteria, especially antibiotic-producing bacteria, and that the detoxification pathway is dependent on in vivo production of a protein acyl glucosaminyl inositol amidase by such bacteria. However, pathogenic actinomycetes (that do not produce an antibiotic) also contain a gene encoding an acyl glucosaminyl inositol amidase that becomes activated in the presence of antibiotics administered to a host, for example in treatment of a disease caused by the pathogenic actinomycetes. Thus, the gene(s) encoding the amidases are a family of antibiotic-resistance genes.

More particularly, it is known that mycothiol (1-D-myo-inosityl-2-(N-acetylcysteinyl)amido-2-deoxy-α-D-glucopyranoside) (MSH) is present in a variety of *actinomycetes* and plays an essential role in a pathway of detoxification in such bacteria. Mycothiol is comprised of N-acetylcysteine (Ac-Cys) amide linked to 1-D-myo-inosityl-2-amino-2-deoxy-α-D-glucopyranoside (GlcN-Ins) and is the major thiol produced by most *actinomycetes*. In the mycothiol-dependent detoxification process in *actinomycetes*, an alkylating agent is converted to a S-conjugate of mycothiol, the matter is cleaved to release a mercapturic acid, and the mercapturic acid is excreted from the cell. A subset of the acyl glucosaminyl inositol amidases are referred to herein as S-conjugate amidases, whose substrate is an S-conjugate containing amide. As used herein, the term "S-conjugate" means that the molecule is a thioether or thioester containing two chemical moieties joined by a sulfur (i.e., —S—) moiety. In a preferred embodiment the S-conjugate molecule is derived from mycothiol (FIG. 1A) by the reaction shown in FIG. 1B, wherein RX is an electrophile and R is an alkyl or alkyloid moiety. However, the acyl glucosaminyl inositol amidases do not require a sulfur-containing amide substrate and instead cleave an GlcN-Ins-containing amide substrate.

A mycothiol S-conjugate amidase responsible for cleavage of the S-conjugate of mycothiol in mycothiol-producing bacteria has been purified from *M. smegmatis* and identified as an ortholog of open reading frame Rv1082 in the genome of *M. tuberculosis*. The Sanger Centre annotation of this gene places it at nucleic acid residues 1206520 to 1207383 of the *M. tuberculosis* genome. It codes for a protein of 288 amino acid residues having an identical N-terminal amino acid sequence to that determined for *M. smegmatis*. Homologous amidases have been identified in *M. leprae* and *M. avium*. The *M. leprae* homolog (ML2391) is coded by nucleic acid residues 2861602 to 2862474 and is 86% identical to Rv1082 (Sangre Centre). The *M. avium* homolog is coded by nucleic acid residues 1152499 to 1153362 and is 84% identical to Rv1082 (TIGR—The Institute for Genomic Research). An additional S-conjugate amidase homolog has been identified in the *M. bovis* genome and is 99% identical to Rv1082 (Sanger Centre). Genes encoding mycothiol S-conjugate amidase appear to be present in all mycobacterial genomes and it seems likely that homologs will be found in other mycothiol-producing *actinomycetes*.

In addition, most of the homologous non-mycobacterial proteins are found in actinomycetes that produce mycothiol. It is known that homolog genes encoding S-conjugate amidases are found within antibiotic synthesis operons of the antibiotic producers *Streptomyces lincolnensis, Amycolatopsis mediterranei, Amycolatopsis orientalis, Streptomyces lavendulae, Streptomyces coelicolor, Streptomyces rochei*, and the polyketide erythromycin antibiotic producer *Saccharopolyspora erythraea*. Two other bacteria, *Corynebacterium diphtheria* and *Deinococcus radiodurans*, also encode acyl glucosaminyl inositol amidase homologs. Four of these open reading frames are putative *actinomycetes* proteins encoded within the lincomycin, erythromycin, mitomycin and the rifamycin antibiotic biosynthetic operons.

At least four major domains are highly conserved among known bacterial acyl glucosaminyl inositol amidase homologs and three out of the four domains contain conserved histidine residues. These conserved domains are thought to be involved in the amide hydrolysis and binding to glucosaminyl inositol. The histidine residues are though to contribute to binding of a zinc ($Zn^{2+}$) metal ion in the enzyme. Members of the family of acyl glucosaminyl inositol amidase proteins are highly conserved and share a high degree of identity throughout the amino-terminal half.

Figure 1C:
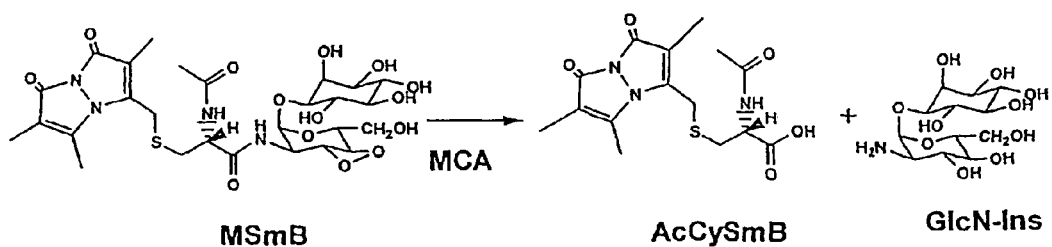
FIG. 1C is a schematic representation showing hydrolysis of bimane derivative (MSmB) formed by alkylation of mycothiol by monobromobimane (mBBr), which is cleaved to produce GlcN-Ins and the bimane derivative of N-acetylcysteine (AcCySmB), a mercapturic acid.

Thus, it is known in the art that acyl glucosaminyl inositol amidases are formed in vivo by bacteria as part of a detoxification pathway, usually in antibiotic-producing bacteria, and most usually in bacteria characterized by intracellular production of mycothiol. An assay for determining amidase activity of such acyl glucosaminyl inositol amidases involves treatment of the amidase producing bacterium with the alkylating agent monobromobimane (mBBr), causing the cellular mycothiol to be converted to its bimane derivative (MSmB) (FIG. 1C). The latter is rapidly cleaved to produce GlcN-Ins and the bimane derivative of N-acetylcysteine (AcCySmB), a mercapturic acid that was rapidly exported from the cells into the medium. The other product of cleavage, GlcN-Ins, is retained in the cell and utilized in the resynthesis of mycothiol.

A similar in vitro assay utilizing acyl glucosaminyl inositol amidase obtained by purification from a mycothiol-producing bacterium, such as *M. smegmatis* or *M. tuberculosis* is readily used to screen compounds to determine those that inhibit amidase activity of the amidases. In this assay, mycothiol is alkylated with mBBr to produce the stable, fluorescent derivative MSmB, which can be quantitated by HPLC using known methods and as illustrated in the Examples herein. Mycothiol is easily isolated from *M. smegmatis* and can be converted quantitatively to MSmB in minutes for use in this assay (See Example 2). Alternatively, recombinant *M. tuberculosis* MCA can be over-expressed in a host cell, such as *E. coli*, for use as the enzyme. A synthetic bimane derivative of *M. tuberculosis* MCA can be prepared as described in Example 2 for use in the invention assay methods. Exposure of a pure sample of MSmB to an acyl glucosaminyl inositol amidase results in the production of a substantial amount of the breakdown product AcCySmB, indicating that MSmB is cleaved by the acyl glucosaminyl inositol amidase. When the pure sample of MsmB and acyl glucosaminyl inositol amidase is exposed to a cell free extract of an organism that produces an invention naturally occurring inhibitor of the acyl glucosaminyl inositol amidase acyl glucosaminyl inositol amidase the substantial absence of, or reduction in, the amount of the fluorescent mycothiol derivative obtained due to activity of the amidase indicates that the organism from which the extract was prepared naturally produces an inhibitor of acyl glucosaminyl inositol amidase. Samples of the incubation mixture can also be analyzed at intervals for production of the other potential product of MSmB cleavage, GlcN-Ins, as well as for MSmB and AcCySmB. In the absence of an inhibitor, at >50% conversion approximately 1.0 equivalent of MSmB (0.1 nmol) yields 1.00±0.02 equivalent of AcCySmB and 0.80±0.08 equivalent of GlcN-Ins with the reaction proceeding to 97% conversion of MSmB in 60 min at 23° C. Any substantial reduction in this conversion rate indicates inhibitory action of a naturally occurring compound produced by the test organism and present in the test extract.

Detection of the fluorescent breakdown product AcCySmB is readily made by any method known in the art for detection of fluorescence. A fluorescence detected-HPLC assay for this breakdown product of MsmB is well known (G. L. Newton et al., 2000a supra) (See also copending U.S. patent application Ser. No. 09/733,569, filed Dec. 7, 2000, which is incorporated herein by reference in its entirety. For acyl glucosaminyl inositol amides which to not contain cysteine a fluorescence detected-HPLC assay for the breakdown product GlcN-Ins is well known (G. L. Newton, et al., 2000b supra)(See also copending U.S. patent application Ser. No. 10/297,512 filed Aug. 16, 2004) which is incorporated herein by reference in its entirety.

mBBr is also known to penetrate cells rapidly and to convert intracellular thiols (e.g., mycothiol) to their bimane derivatives (Newton, et al. (1995) supra.). Thus the test for inhibitory action of a naturally occurring compound obtained from a cell extract can also be conducted in an in vivo assay to determine whether a test compound is effective as an inhibitor of acyl glucosaminyl inositol amidase activity in vivo by exposing a cultured strain of live mycothiol-producing bacterial cells to a purified test compound and assaying the inhibitory effect of the purified test inhibitor upon the mycothiol production pathway in the mycothiol-producing bacterium. An interruption in the production of mycothiol in the test bacteria causes inhibition of growth and even death. Generally, it is most convenient to conduct such an in vivo assay by culturing the mycothiol-containing bacteria in the presence of the test compound and an antibiotic. Disruption in the mycothiol-producing pathway and in the mycothiol-dependent detoxification pathway in the bacterium caused by inhibitory activity of the test compound on the amidases in the bacterium will interrupt the natural resistance to the antibiotic and other alkylating agents, and the like, provided by mycothiol in the bacterium. Antibiotics useful for this purpose inositol amidase. A preliminary screen of the extract of a specimen of Oceanapia sp.7 showed strong activity against MCA, as determined by the absence of the MCA/MSH cleavage product AcCys-bimane in a fluorescence-detected HPLC assay (G. L. Newton et al. 2000, supra). Bioassay-guided purification of the MeOH/10% $H_2O$ soluble material by reverse-phase (C18) chromatography, followed by chromatography on LH20 (eluting with MeOH), yielded known compounds pseudoceratine (A. Benharref and M. Pais, *J. Nat. Prod.* (1996) 59:177)(compound 2, 24.7 mg, 1.40%) and uranidine (G. Cimino et al. *Tetrahedron Lett.* (1984) 25:2925) (17.7 mg, 1.0%) and a small amount of compound 1 (2 mg, 0.11%). Compounds are numbered as shown in Table 1 below.

In this assay, Compounds 1, 2, 4 and 6 (Table No. 1) inhibited mycothiol S-conjugate amidase by 50% at 2, 100, 3, and 37 µM, respectively, but uranidine was ineffective. Compound 1 exhibited the strongest inhibition of MCA, but initial efforts to establish the structure were hampered by extensive decomposition upon reverse-phase HPLC. Elucidation of the structure of Compounds 1 and 6 is described in Example 1 below.

Figure 2:
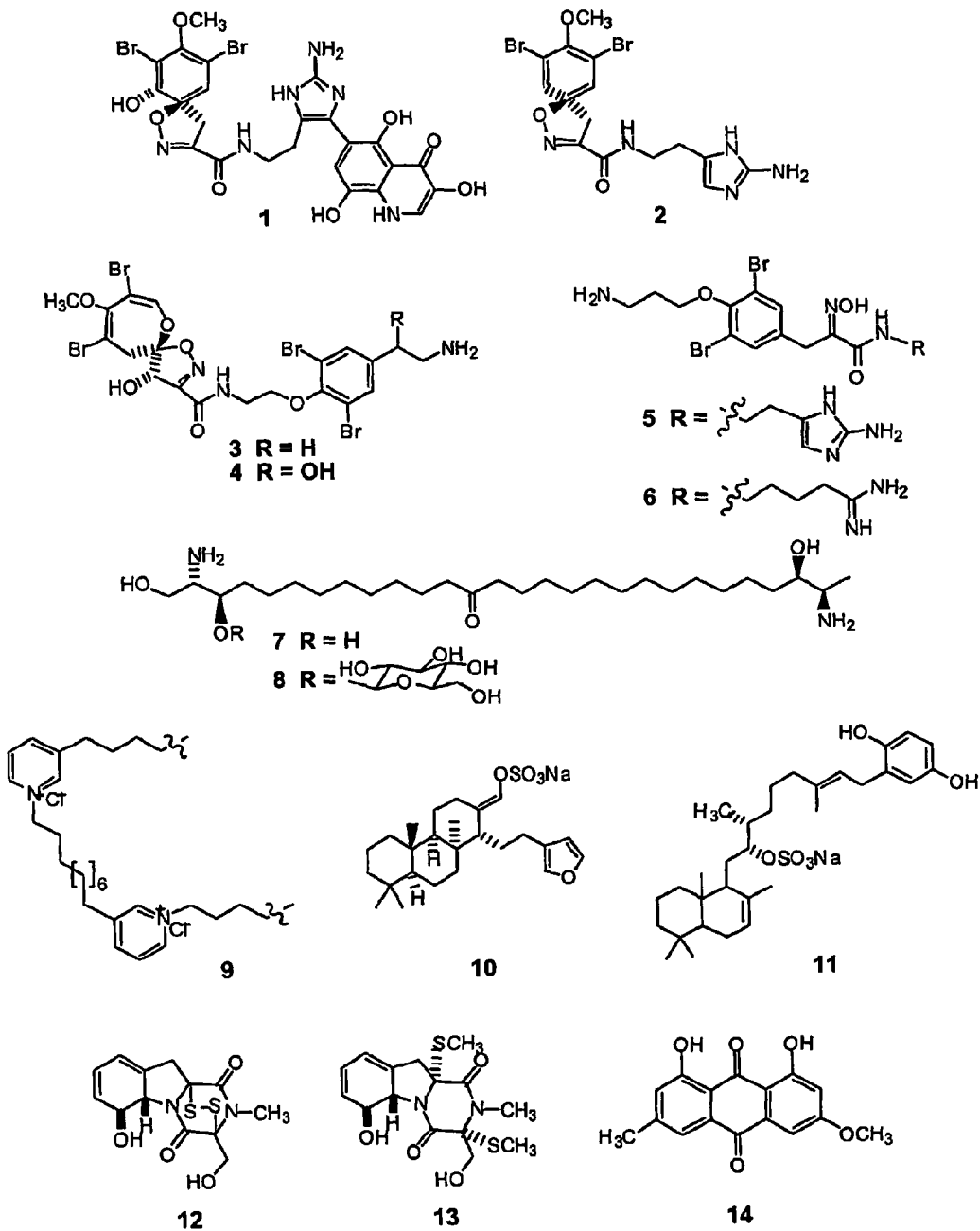
FIG. 2 is a compilation showing the chemical structures of invention acyl glucosaminyl inositol amidase inhibitors Compounds 1 through 14.
Figure 3A:
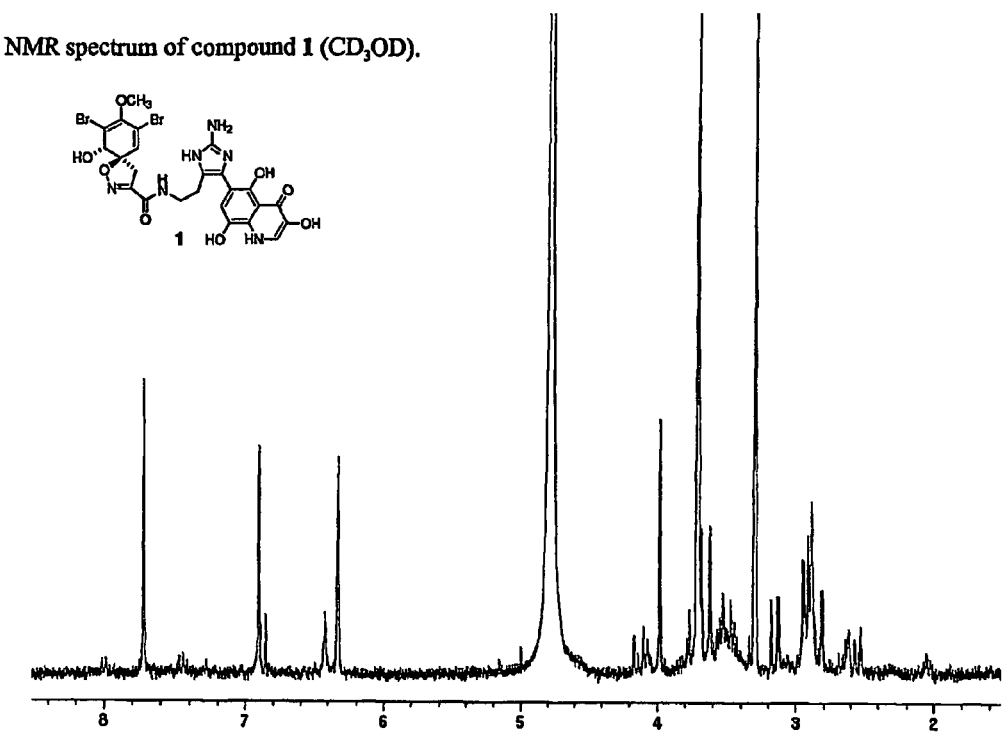
FIGS. 3A and 3B are graphs showing $^1H$ and $^{13}C$ NMR spectra of compound 1 in $CD_3OD$ run on a Mercury300 spectrometer.
Figure 3B:
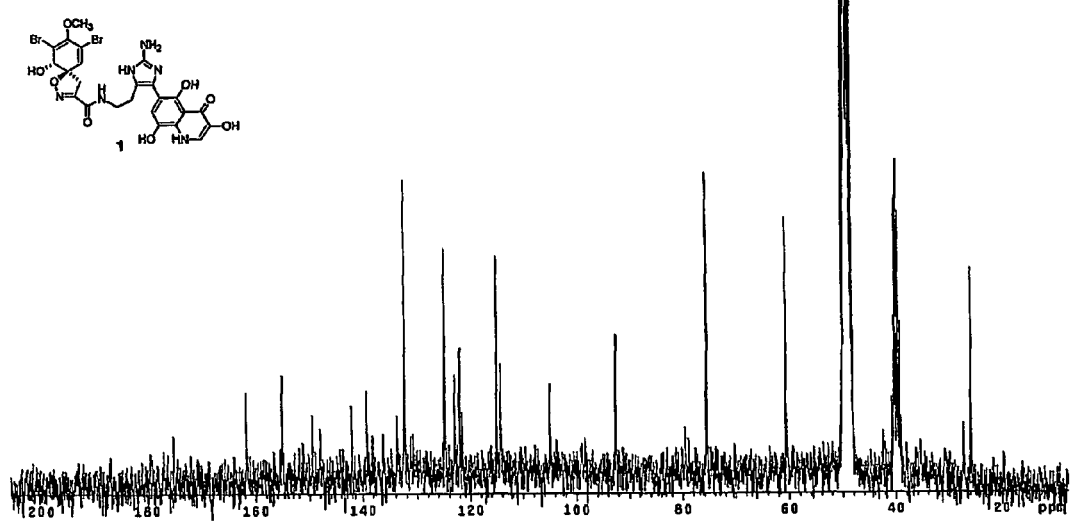
Figure 4:
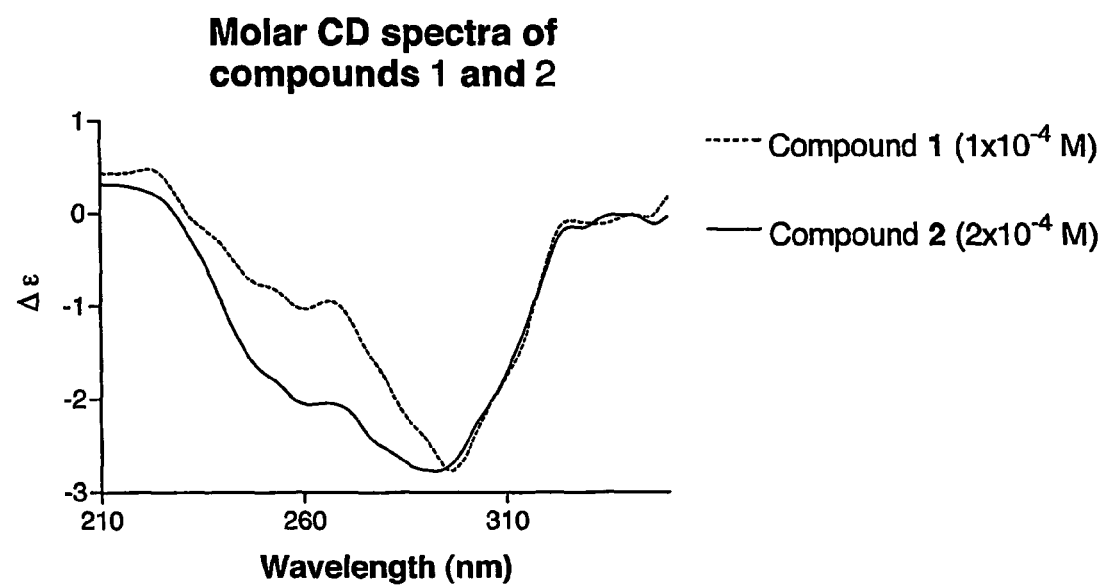
FIG. 4 is a graph showing CD spectra of compounds 1 and 2 run on a Jasco-700 spectropolarimeter in $CH_3OH$.
Figure 5:
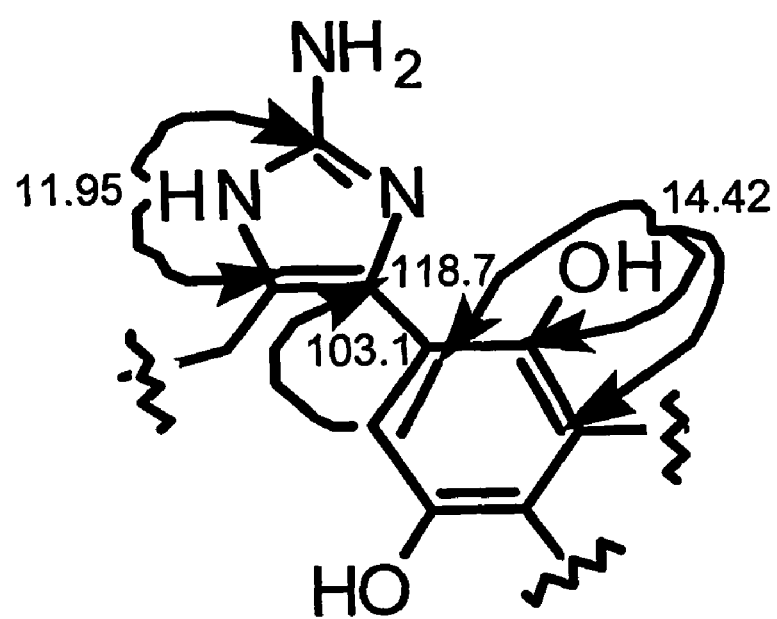
FIG. 5 is a schematic drawing showing the correlation that establishes the connection between the 2-amino imidizolyl and quinolinone fragments of Compound 1.

Based on the results of these studies, further cell extracts of marine sponges and terrestrial fungus were assayed to determine those that contained inhibitors of acyl glucosaminyl inositol amidases and corresponding inhibitors were purified from the cell extracts to yield the additional compounds shown in Table 1 and as described in Example 2 herein. The chemical structures of Compounds 1-14 are shown in FIG. 2 herein.

| Compound | Ref. | or reference | Organism | Genus | Collection No. | M. tb | M. smeg |
|---|---|---|---|---|---|---|---|
| 1 | 1 | Nicholas et al. | Marine sponge | Oceanapia sp. | C2385 | 3 | 2 |
| 2 | 2 | Pseudoceratine | " | Oceanapia sp. | C2385 | 100 | 100 |
| 3 | 3 | psammaplysin A | " | Pseudoceratina sp. | C16115 | 30 | 30 |
| 4 | 3 | psammaplysin B | " | Pseudoceratina sp. | C16115 | 30 | 20 |
| 5 | 4 | Litaudon & Guyot | " | Oceanapia sp. | C2385 | 30 | 37 |
| 6 | 1 | Nicholas et al. | " | Oceanapia sp. | C2385 | 10 | 3 |
| 7 | 5 | Oceanapiside | " | Oceanapia sp. | C2523 | 10 | 0.5 |
| 8 | | oceanapiside aglycon | " | Aglycon of 7 | C2523 | 20 | 5 |
| 9 | 6 | 1,3-pyridinium polymers | " | Amphimedon sp. | C2355 | 0.1 | 0.1 |
| 10 | 7 | Suvanine | " | Coscinoderma matthewsi | C16199 | nt | 60 |
| 11 | 8 | halisulfate 1 | " | Coscinoderma matthewsi | C16199 | nt | 40 |
| 12 | | Gliotoxin | Terrestrial fungus | Mycena sp. | F205435 | 30 | 30 |
| 13 | | S,S-dimethyl gliotoxin | " | Aspergillus sp. | F205337 | nt | 280 |
| 14 | | Physcion | " | Aspergillus sp. | F205337 | nt | 50 |

References.
1. Nicholas, G. M.; Newton, G. L.; Fahey, R. C.; Bewley, C. A. Org. Lett. 2001, 3, 1543.
2. Benharref, A. and Pais, M. J. Nat. Prod. 1996, 59, 177.
3. Roll, D. M.; Chang, C. W. J.; Scheuer, P. J.; Gray, G. A.; Shoolery, J. N.; Matsumoto, G. K.; Van Duyne, G. D.; Clardy, J. C. J Am Chem Soc. 1985, 107, 2916.
4. Litaudon, M.; Guyot, M. Tetrahedron Lett 1986, 27, 4455.
5. Nicholas; G. M.; Hong, T. W.; Molinski, T. F.; Lerch, M. L; Cancilla, M. T.; Lebrilla, C. B. J. Nat. Prod. 1999, 62, 1679.
6. Davies-Coleman, M. T.; Faulkner, D. J.; Dubowchik, G. M.; Roth, G. P.; Polson, C.; Fairchild, C. J. Org. Chem. 1993, 58, 5925.
7. Manes, L. V.; Crews, P.; Kernan, M. R.; Faulkner, D. J.; Fronczek, F. R.; Candour R. D. J. Org. Chem. 1988, 53, 570.
8. Kernan, M. R. and Faulker, D. J. J. Org. Chem. 1988, 53, 4574.

include such antibiotics as cerulenin, erythromycin, exfoliamycin, granaticin, kinamycin, lincomycin, mitomycin, naphthomycins, rifamycins, streptothricins, and vancomycin group antibiotics.

In the present invention, cell extracts of organisms have been screened using the above-described in vitro assay to discover small molecule inhibitors of acyl glucosaminyl Thus, in another embodiment, the present invention provides methods for Identifying a naturally occurring inhibitor of acyl glucosaminyl inositol amidase activity by contacting a candidate cell extract of an organism with an acyl glucosaminyl inositol amidase or a polynucleotide encoding the amidase in the presence of an GlcN-Ins-containing amide under suitable conditions and determining the presence or absence of breakdown products of the amide indicative of amide hydrolase activity. The substantial absence of the amide hydrolase activity is indicative that the organism produces a naturally occurring compound that inhibits activity of the amidase. For example, if the amidase is an S-conjugate amidase, the absence of mercapturic acid (AcCysR) and/or GlcN-Ins as breakdown products indicates the candidate compound is an inhibitor of the S-conjugate amidase. Suitable conditions include those as known in the art and as described herein. The method can further comprising purifying the naturally occurring compound with inhibitory activity from the cell extract, using methods known in the art and as described herein in the Examples.

When administered in treatment of a disease associated with infection of the subject with a pathogenic bacteria that produces a native acyl glucosaminyl inositol amidase in conjunction with an antibiotic (i.e., in combination therapy) the invention inhibitors increase the therapeutic effect of the antibiotic, for example by decreasing both virulence and antibiotic resistance of the pathogen.

Preferably, the inhibitor of acyl glucosaminyl inositol amidase is a compound that inhibits intracellular production of mycothiol. For example, in one embodiment, the candidate compound inhibits intracellular activity of the acyl glucosaminyl inositol amidase.

In yet another embodiment according to the present invention, there are provided methods for decreasing the antibiotic-resistance of pathogenic GlcN-Ins-amidase producing bacteria by introducing into the bacteria an invention inhibitor of acyl glucosaminyl inositol amidase activity. The intracellular presence of the invention inhibitor decreases activity of the amidase, thereby decreasing the antibiotic-resistance of the bacteria as compared with untreated control bacteria Preferably, the inhibitor inhibits intracellular production of the amidase. The inhibitor can be "introduced into" the bacteria by incubating the bacteria with the inhibitor.

Preferably, the pathogenic bacteria treated to reduce antibiotic resistance according to the invention methods are *actinomycetes*, such as *M. smegmatis, M. tuberculosis, M. leprae, M. bovis* BCG. *M. intracellulare, M. africanum, M. marinarum, M. chelonai, Corynebacterium diphtheria, Actinomycetes israelii, M. avium*, and the like.

The amidase used to test the inhibitory effect of a putative inhibitor of the invention can be obtained in a number of ways known in the art. For example, as described above, the acyl glucosaminyl inositol amidase can be purified from a bacteria that naturally produces such an enzyme, for example a mycothiol S-conjugate amidase, e.g. one capable of hydrolyzing a mycothiol S-conjugate where the S—R group may be an alkyl or alkyloid group to which it is native. Alternatively, the acyl glucosaminyl inositol amidase can be recombinantly produced from genes that encode a naturally occurring protein using methods known in the art. Alternatively, the mycothiol S-conjugate amidase or acyl glucosaminyl inositol amidase used in the invention screening methods may contain conservative variations of the amino acids contained in the naturally occurring amidase.

A "conservative variation" in an amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from an amidase polypeptide, resulting in modification of the structure of the polypeptide, without significantly altering its biological activity. For example, carboxyl-terminal amino acids that are not required for amidase activity can be removed.

Biologically functional viral and plasmid DNA vectors capable of expression and replication in a host useful for recombinant production of the acyl glucosaminyl inositol amidase used to screen for invention inhibitors are known in the art. Such vectors are used to incorporate DNA sequences of the invention. In general, expression vectors containing promoter sequences which facilitate the efficient transcription of the inserted prokaryotic genetic sequence are used in connection with the host. The expression vector typically contains an origin of replication, a promoter, and a terminator, as well as specific genes which are capable of providing phenotypic selection of the transformed cells.

In addition to expression vectors known in the art such as bacterial, yeast and mammalian expression systems, baculovirus vectors may also be used. One advantage to expression of foreign genes in this invertebrate virus expression vector is that it is capable of expression of high levels of recombinant proteins, which are antigenically and functionally similar to their natural counterparts. Baculovirus vectors and the appropriate insect host cells used in conjunction with the vectors will be known to those skilled in the art.

The term "recombinant expression vector" refers to a plasmid, virus or other vehicle known in the art that has been manipulated by insertion or incorporation of the invention acyl glucosaminyl inositol amidase genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XG-PRT, gpt).

The isolation and purification of host cell expressed amidase polypeptides may be by any conventional means such as, for example, preparative chromatographic separations and immunological separations such as those involving the use of monoclonal or polyclonal antibody.

Transformation of the host cell with the recombinant DNA may be carried out by conventional techniques well known to those skilled in the art. Where the host is prokaryotic, such as

*E. coli*, competent cells which are capable of DNA uptake can be prepared from cells harvested after exponential growth and subsequently treated by electroporation or the $CaCl_2$ method using procedures well known in the art. Alternatively, $MgCl_2$ or RbCl could be used.

Where the host used is a eukaryote, various methods of DNA transfer can be used. These include transfection of DNA by calcium phosphate-precipitates, conventional mechanical procedures such as microinjection, insertion of a plasmid encased in liposomes, or the use of virus vectors. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Examples of mammalian host cells include COS, BHK, 293, and CHO cells.

Eukaryotic host cells may also include yeast. For example, DNA can be expressed in yeast by inserting the DNA into appropriate expression vectors and introducing the product into the host cells. Various shuttle vectors for the expression of foreign genes in yeast have been reported (Heinemann, J. et al., Nature, 340:205, 1989; Rose, M. et al., Gene, 60:237, 1987).

The recombinant acyl glucosaminyl inositol amidase polypeptide used to screen naturally occurring inhibitors of acyl glucosaminyl inositol amidase for inhibitory activity can also be a fusion protein further comprising a second polypeptide portion having an amino acid sequence from a protein unrelated to the acyl glucosaminyl inositol amidase. Such fusion proteins can be functional in a two-hybrid assay as is known in the art.

Other features and advantages of the invention will be apparent from the detailed description herein, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the terms "gene", "recombinant gene" and "gene construct" refer to a nucleic acid comprising an open reading frame encoding an invention acyl glucosaminyl inositol amidase, including both exon and (optionally) intron sequences. The term "intron" refers to a DNA sequence present in a given acyl glucosaminyl inositol amidase gene which is not translated into protein and is generally found between exons.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

The term "transfection" or "transforming" and grammatical equivalents thereof, refers to the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA.

"Cells" or "cell cultures" or "recombinant host cells" or "host cells" are often used interchangeably as will be clear from the context. These terms include the immediate subject cell which expresses the cell-cycle regulatory protein of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant acyl glucosaminyl inositol amidase polypeptide.

As used herein, the term "vector" refers to a nucleic acid molecule capable of transporting another nucleic acid to which it has been linked. The term "expression vector" includes plasmids, cosmids or phages capable of synthesizing the subject acyl glucosaminyl inositol amidase polypeptide encoded by the respective recombinant gene carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In preferred embodiments, transcription of a recombinant acyl glucosaminyl inositol amidase gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of the regulatory protein.

As used herein, a "transgenic organism" is any organism, preferably a bacteria in which one or more of the cells of the organism contain heterologous nucleic acid introduced by way of human intervention, such as by transgenic techniques well known in the art. The nucleic acid is introduced into the cell by way of deliberate genetic manipulation, such as by microinjection or by infection with a recombinant virus or a vector. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic organisms described herein, the transgene causes cells to express a recombinant form of the subject acyl glucosaminyl inositol amidase polypeptides.

The term "isolated" or "purified" as also used herein with respect to invention inhibitors of acyl glucosaminyl inositol amidase activity refers to compounds that are substantially free of cellular material or culture medium when purified from cell extracts of naturally occurring organisms or other chemicals when chemically synthesized. Methods of purifying compounds from cell extracts are well known in the art and are further illustrated in the Examples herein.

Isolated nucleic acids which differ from the wild type nucleotide sequences known in the art due to degeneracy in the genetic code can also be used to produce acyl glucosaminyl inositol amidases useful in discovering invention inhibitors. For example, a number of amino acids are designated by more than one triplet. Codons that specify the same amino acid, or synonyms (for example, CAU and CAC are synonyms for histidine) may result in "silent" mutations that do not affect the amino acid sequence of the protein. However, it is expected that DNA sequence polymorphisms that do lead to changes in the amino acid sequences of the subject acyl glucosaminyl inositol amidase polypeptides will exist among prokaryotic cells. One skilled in the art will appreciate that these variations in one or more nucleotides (up to about 3-4% of the nucleotides) of the nucleic acids encoding a particular member of the acyl glucosaminyl inositol amidase polypeptide family may exist among individuals of a given species due to natural allelic variation. Any and all such nucleotide variations and resulting amino acid polymorphisms are within the scope of this invention.

Fragments of the nucleic acid encoding a biologically active portion of the subject acyl glucosaminyl inositol amidase polypeptides can also be used in assays to screen for discovery of additional examples of the invention inhibitors of acyl glucosaminyl inositol amidase. Such fragments encode a peptide which retains at least a portion of the biological activity of the full-length protein (i.e., a peptide capable of acyl glucosaminyl inositol amidase activity) as defined herein.

A nucleic acid encoding a peptide having an activity of a S-conjugate amidase polypeptide may be obtained from mRNA or genomic DNA present in any of a number of antibiotic-producing or pathogenic bacteria described herein, particularly *actinomycetes*, in accordance with protocols generally known to those skilled in the art. A cDNA encoding an acyl glucosaminyl inositol amidase polypeptide, for example, can be obtained by isolating total mRNA from a bacterial cell. Double stranded cDNAs can then be prepared from the total mRNA, and subsequently inserted into a suitable plasmid or bacteriophage vector using any one of a number of known techniques. A gene encoding an acyl glucosaminyl inositol amidase polypeptide can also be cloned using established polymerase chain reaction techniques in accordance with the nucleotide sequence information provided by the invention.

Expression vectors may comprise a nucleotide sequence encoding an acyl glucosaminyl inositol amidase polypeptide operably linked to at least one regulatory sequence. Operably linked is intended to mean that the nucleotide sequence is linked to a regulatory sequence in a manner that allows expression of the nucleotide sequence. Regulatory sequences are art-recognized and are selected to direct expression of the peptide having an activity of an acyl glucosaminyl inositol amidase polypeptide. Accordingly, the term regulatory sequence includes promoters, enhancers and other expression control elements. Exemplary regulatory sequences are described in Goeddel; Gene Expression Technology: Methods in Enzymology 185, Academic Press, San Diego, Calif. (1990). For instance, any of a wide variety of expression control sequences-sequences that control the expression of a DNA sequence when operatively linked to it may be used in these vectors to express DNA sequences encoding the acyl glucosaminyl inositol amidase polypeptides of this invention. Such useful expression control sequences, include, for example, the early and late promoters of SV40, adenovirus or cytomegaloviums immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast .alpha.-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

As will be apparent, such gene constructs can be used to cause expression of the subject acyl glucosaminyl inositol amidase polypeptides in cells propagated in culture, e.g. to produce proteins or peptides, including fusion proteins or peptides, for purification and subsequent use in assays intended to screen for inhibitors of their amidase activity.

The acyl glucosaminyl inositol amidase polypeptides used to screen for detection of inhibitors of acyl glucosaminyl inositol amidase activity may also be produced by transfection of a host cell with expression vector encoding one of the subject acyl glucosaminyl inositol amidase polypeptide and cultured under appropriate conditions to allow expression of the peptide to occur. The peptide may be secreted and isolated from a mixture of cells and medium containing the peptide. Alternatively, the peptide may be retained cytoplasmically and the cells harvested, lysed and the protein isolated. A cell culture includes host cells, media and other byproducts. Suitable media for cell culture are well known in the art. The peptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for particular epitopes of the subject acyl glucosaminyl inositol amidase polypeptides.

The invention will be further described with reference to the following examples; however, it is to be understood that the invention is not limited to such examples.

EXAMPLE 1

General Procedures

UV spectra were obtained using a Beckman DU-600 spectrophotometer; optical rotations were measured on a Perkin Elmer 341 polarimeter in $CH_3OH$; CD spectra were measured on a Jasco-700 spectropolarimeter using a 0.2 cm cell; IR spectra were obtained with a Bio-Rad-FTS-45 FT-IR spectrophotometer. Low- and high-resolution fast atom bombardment mass spectra were obtained on a Jeol-SX102 instrument. Reverse-phase (C18) HPLC was carried out using a GBC LC1150 pump, a GBC LC5100 photodiode array detector and a Waters μBONDAPAK™ C18 column (7.8×300 mm) at a flow rate of 3 mL/min.

1-D NMR spectra were recorded on A Varian Mercury 300 and 2-D NMR spectra at 27° C. on a Bruker DMX500 and referenced to residual solvent DMSO $d_6$, $\delta_C$ 39.5, $\delta_H$ 2.50). Protons were assigned from $^1H$ NM or HSQC spectra.

An extract of a specimen of Oceanapia sp.7 was obtained from the NCI open repository.

A preliminary screen of the extract showed strong inhibitory activity against MCA, as determined by the absence of the MCA/MSH cleavage product AcCys-bimane (AcCysBm) in a fluorescence-detected HPLC assay using 50 μM MSmB as substrate and conducted as previously described. Bioassay-guided purification of the MeOH/10% $H_2O$ soluble material from the Oceanapia sp.7 extract by reverse-phase (C18) chromatography, followed by chromatography on LH20 (eluting with MeOH), yielded known compounds pseudoceratine (A. Benharref and M. Pais, *J. Nat. Prod.* (1996) 59:177) (compound 2, 24.7 mg, 1.4%) and uranidine (G. Cimino et al. *Tetrahedron Lett.* (1984) 25:2925) (17.7 mg, 1.0%) and a small amount of compound 1 (2 mg, 0.11%).

Further assays were performed to determine inhibitory effect of Compounds 1, 2, 5, 6 and uranidine on mycothiol S-conjugate amidase using the above described assay. The results of these assays showed that Compounds 1, 2, 5 and 6 inhibited the mycothiol S-conjugate amidase by 50% at 2, 100, 3, and 37 μM, respectively, but uranidine was ineffective. Compound 1 exhibited the strongest inhibition of MCA, but initial efforts to establish the structure were hampered by extensive decomposition upon reverse-phase HPLC with $CH_3CN/H_2O$ (0.05% trifluoroacetic acid (TFA)).

Purification of a second MeOH/10% $H_2O$ soluble fraction of the crude extract of *Oceanapia* sp.7 by LH20 chromatography (MeOH) alone provided increased amounts of compound 1 (6.0 mg 0.24%). Repeated reverse-phase (C18) HPLC of other fractions from this LH20 column gave compounds 6 (2.0 mg, 0.11%) and 5 (1.5 mg, 0.08%). Compound 1 showed an isotopic cluster of MH+ ions in the ratio of 1:2:1 in the FABMS at m/z 681, 683, and 685. A molecular formula of $C_{24}H_{22}O_8N_6Br_2$ was determined by high-resolution fast atomic bombardment mass spectrometry (HRFABMS).

An initial comparison of the $^1H$ and $^{13}C$ NMR spectra of compound 1 showed obvious similarities with the spectra for compounds 2 and uranidine and indicated that the dibrominated cyclohexadienol-spiro-isoxazoline system was intact. This was confirmed by HSQC and HMBC 2D NMR experiments (Table 2). The spin system from C9 to C11 was assigned by HMBC correlations from the methylene protons at $\delta_H$ 3.40 (H10) and the exchangeable proton at $\delta_H$ 8.62 (C9-NH) to the amide carbon at C9 ($\delta_C$ 158.9), along with TOCSY correlations between these protons and the second methylene at $\delta_H$ 2.75 (H11). In elucidating the complete structure of 1, HMBC correlations from H11 ($\delta_H$ 2.75) to two aromatic quaternary carbons at $\delta_C$ 120.4 (C12) and 118.7 (C13) and from an exchangeable proton at $\delta_H$ 11.95 (12-NH) to the carbons at $\delta_C$ 120.4 (C12) and 146.2 (C14) were critical for the analysis (FIG. 1). For the imidazolyl-quinolinone portion of compound 1, all but two of the proton and carbon resonances were consistent with those reported for uranidine (Cimino et al., supra) and were supported by HMBC correlations (G. Cimino et al. *Tetrahedron Lett.* (1984) 25:2925). Notable differences included the absence of the resonances corresponding to H6 and H7 in uranidine and the appearance of a singlet at $\delta_H$ 6.96. This new singlet was assigned as H7' in compound 1 on the basis of observed HMBC correlations to carbons at $\delta_C$ 128.9 (8a'), 137.0 (C8'), and 149.3 (C5'), confirming substitution at the C6' carbon. Analysis of HMBC spectra recorded with varying values of Δt (set to observe long-range $^1H$-$^{13}C$ couplings of 6, 8, 13, and 20 Hz) allowed the detection of correlations from the hydrogen-bonded hydroxyl proton at $\delta_H$ 14.42 (5'-OH) to three aromatic carbons at $\delta_C$ 112.2, 149.3, and 103.1, which were assigned as C4a',C5', and C6', respectively. An HMBC correlation from H7' (δH 6.96) to a quaternary carbon at $\delta_C$ 118.7 (C13) gave the last carbon-carbon connection and linked together the quinolinone and imidazole subunits (FIG. 1). Full NMR data are presented in Table 2 below.

The absolute stereochemistry of compound 1 was determined by comparing the spectral data with those of compound 2 and its enantiomer. Both enantiomers of compound 2 have been described, and the absolute stereochemistry has been determined by comparing CD spectra with previously published data (A. Benharref et al. *Tetrahedron Lett.* (1984) 25:2925 and J. Kobayashi et al. *Chem. Pharm. Bull.* (1995) 43:463). On the basis of these studies, the specific rotation and the negative Cotton effect observed in the CD spectrum for compound 2 confirmed it to be the levorotatory enantiomer, pseudoceratine, with absolute configuration 1-(S), 6-(R). Comparison of the $^1H$ NMR chemical shifts for H1, H7a, and H7b of compounds 1 and 2 indicated that they have the same relative stereochemistry. Thus the negative Cotton effect in the CD spectrum for compound 1 indicated that it also has the absolute configuration 1-(S), 6-(R) (Kobayashi et al., supra).

The $^1H$ and $^{13}C$ NMR data for Compound 5 were consistent with those reported previously for a compound having the common name psammaplysin B (M Litaudon and M. Guyot *Tetrahedron Lett.* (1986) 27:4455). A molecular formula of $C_{17}H_{26}N_6O_3Br_2$ for compound 6 was determined by HR-FABMS as shown below. The obvious similarities in the $^1H$ NMR spectra of compounds 5 and 6 were the presence of the aromatic singlet at $\delta^H$ 7.49 (H2 and H6), the methylene signals corresponding to H15-H17, and the singlet at $\delta^H$ 3.82 (H7). In contrast, the $^1H$ NMR spectrum of Compound 6 lacked the methylenes corresponding to C10 and C11 of Compound 5 and the aromatic signal at $\delta^H$ 6.51 (H13). From the HMBC and COSY spectra of Compound 6 a chain of four methylenes, H10-H13 ($\delta^H$ 3.27, 1.56 (2CH$_2$) and 3.17), ending with a guanidine group (C14, $\delta_C$ 156.8) was evident. These carbon and proton resonances are consistent with those reported for other compounds that contain this fragment (Kobayashi et al., supra).

Compounds 1 and 6 are novel. Compound 1 contains a rare example of an amino-imidazole coupled to another aromatic substitutent; a second example occurs in the histidino-tyrosine bridge of the bicyclic glycopeptidolipids aciculitins A-C (C. A. Bewley et al., *J. Am. Chem. Soc.* (1996) 118: 4314). With the exception of this example, bromo-tyrosine-derived metabolites have been limited exclusively to sponges of the order Verongida and arguably exemplify the most solid chemotaxonomic grouping among the Porifera. While a voucher specimen corresponding to the sponge from which compounds 1, 2, 5 and 6 were obtained was reidentified as an Oceanapia sp., it remains possible that a sample of verongid sponge was present in the actual collection.

Compounds 1, 2, 5, and 6 are the first examples of natural products that inhibit an enzyme central to a mycothiol-dependent detoxification pathway found in mycobacteria.

Compound 1.

$^1$H NMR (CD$_3$OD, 300 MHz) 7.72 (s, H2'), 6.90 (s, H7'), 6.33 (s, H5), 3.98 (br s, H1), 3.70 (s, H15), 3.64 (d, J=18.0 Hz, H7b), 3.50 (m, H10), 2.92 (d, J=17.7 Hz, H7a), 2.91 (m, H11).

$^{13}$C NMR (CD$_3$OD, 75 MHz) $\delta_C$ 175.0 (C4'), 161.7 (C9), 155.0 (C8), 151.5 (C5'), 149.4 (C3), 147.9 (C14), 141.9, 139.1, 133.7, 132.3 (C5), 124.8 (C2'), 122.9 (C4), 121.9, 121.5, 114.9 (C7'), 114.3, 114.2, 104.9 (C6'), 92.4 (C6), 75.5 (C1), 60.5 (C15), 40.0 (C7), 39.6 (C10), 25.7 (C11).

IR (ZnSe, film) 3166 (broad), 1715, 1694, 1679, 1674, 4653, 1588, 1557, 1539, 1438, 1263, 1219, 1025, 994 cm$^{-1}$ Table 2 below summarizes the full NMR data for compound 1, including data obtained from the COSY, HMBC, and ROESY spectra in DMSO-d$_6$.

TABLE 2

| Atom | $\delta_C$ | $\delta_H$, multiplicity, J (Hz)$^a$ | COSY | HMBC (20 Hz) | HMBC (13 Hz) | HMBC (8 Hz) | ROESY |
|---|---|---|---|---|---|---|---|
| 1 | 73.5 | 3.89, d, 0.6 | | 147.1, 131.2, 113.1, 90.1 | 147.1, 131.2, 113.1, 90.1 | 147.1, 131.2, 113.1, 90.1 | 6.42, 3.60 |
| 2 | 113.1 | | | | | | |
| 3 | 147.1 | | | | | | |
| 4 | 120.8 | | | | | | |
| 5 | 131.2 | 6.56, d, 0.6 | | 147.1, 120.8, 73.5 | 147.1, 120.8, 113.1, 73.5, 39.4 | 147.1, 120.8, 113.1, 90.1, 73.5, 39.4 | 3.12 |
| 6 | 90.1 | | | | | | |
| 7a | 39.4 | 3.12, d, 18.0 | 3.60 | 131.2 | 154.4, 131.2, 90.1, 73.5 | 131.2, 90.1, 73.5 | 6.56 |
| 7b | | 3.60, - | 3.12 | -- | 154.4, 131.2, 90.1, 73.5 | 73.5 weak | 8.62, 3.89 |
| 8 | 154.4 | | | | | | |
| 9 | 158.9 | | | | | | |
| 10 | 38.1 | 3.40, - | 8.62, 2.75 | -- | -- | 120.4, 158.9 (weak) | 8.62 |
| 11 | 24.6 | 2.75, m | 3.40 | 120.4, 38.1 | 120.4 | 120.4, 118.7 | 8.62, 6.96 |
| 12 | 120.4 | | | | | | |
| 13 | 118.7 | | | | | | |
| 14 | 146.2 | | | | | | |
| 15 | 59.6 | 3.69, s | | 147.1 | 147.1 | 147.1 | -- |
| 2' | 124.2 | 7.70, s | | 173.2, 128.9 | 173.2, 128.9 | 173.2, 128.9 | 11.81, 9.00 |
| 3' | 137.7 | | | | | | |
| 4' | 173.2 | | | | | | |
| 4a' | 112.2 | | | | | | |
| 5' | 149.3 | | | | | | |
| 6' | 103.1 | | | | | | |
| 7' | 113.8 | 6.96, s | | 149.3, 128.9, 118.7 | 137.0 | 137.0 | 10.36, 8.62 |
| 8' | 137.0 | | | | | | |
| 8a' | 128.9 | | | | | | |
| 1-OH | | 6.42, br s | | -- | 113.8 | -- | 3.89, 3.60 |
| 9-NH | | 8.62, br t, 5.7 | 3.40 | 158.9, 38.1 | 158.9 | 158.9 | 2.75, 3.12, 6.96 |
| 12-NH | | 11.95, br s | | -- | 146.2, 120.4 | -- | 7.27 |
| 14-NH$_2$ | | 7.27, br s | | -- | -- | -- | 11.95 |
| 1'-NH | | 9.00, br s | | -- | -- | -- | 7.67 |
| 3'-OH | | 11.81, br s | | -- | 139.9, 124.2, 112.2 | -- | 7.67 |
| 5'-OH | | 14.42, br s | | 149.3, 112.2, 103.1 | 149.3, 112.2 | -- | -- |
| 8'-OH | | 10.36, br s | | -- | 128.9 | -- | 6.96 |

$^a$s = singlet, d = doublet, m = multiplet, br = broad, (--) = overlapped.

EXAMPLE 2

Utilizing the procedures described above in Example 1, additional naturally occurring compounds purified from extracts of marine sponge and terrestrial fungus obtained from the NCI Collection were tested for activity as inhibitors of acyl glucosaminyl inositol amidase and purified from cell extracts as described in Example 1.

To quantify the inhibition activity of the purified naturally occurring compounds, $IC_{50}$ values for the invention mycothiol-S-conjugate amidase inhibitors were determined as follows. Fluorescence-based HPLC assays were conducted as described previously using the following reagents. For determining $IC_{50}$ values for *Mycobacterium smegmatis* mycothiol-S-conjugate (MCA), natural mycothiol bimane MSmB) was employed as the substrate, and wild type MCA isolated from cultures of *M. smegmatis* was used for MSmB cleavage. For determining $IC_{50}$ values for *M. tuberculosis* MCA, synthetic MSmB prepared as described by G. M. Nicholas et al. *J. Am. Chem. Soc.* (2002), In press, the article and supplementary material have been published on the world wide web WWW at the url "pubs.acs.org/CHECKCCIP-017071253/isubscribe/journals/jacsat/asap/pdf/ja017891a.pdf" and the url "pubs.acs.org/subscribe/journals/jacsat/suppinfo/ja017891a/ja017891a_s1.pdf") was used as the substrate and recombinant *M. tuberculosis* MCA overexpressed in *Escherichia coli* was used as the enzyme. The recombinant *M. tuberculosis* MCA was subcloned from total genomic DNA isolated from *M. tuberculosis* (H37Rv) (Quiagen Kit), and inserted into a Protein G fusion vector (C. A. Bewley et al. *Prot. Sci.* (1997) 5:2359-2364) originally constructed from a pET-11a vector. The Mtb-MCA-encoding plasmid, referred to as cb-G1082-Mtb, was used to obtain recombinant Mtb-MCA as previously described.

Stock solutions of inhibitors were prepared in MeOH in concentrations ranging from 1-20 mM, depending on availability of compounds. Serial dilutions were made for each inhibitor so that 2 µL of inhibitor were added to each well of substrate to give the final desired inhibitor concentration. All assays were conducted using 30 µM natural or synthetic MSmB and approximately 20 nM natural or recombinant MCA in the presence of varying concentrations of inhibitor. Cleavage reactions were carried out for 20 min. at 31° C., conditions that are well within the initial linear velocity of the enzyme. Enzyme solutions were quantitated using the Bradford method and by UV/Vis spectroscopy.) $IC_{50}$ values were obtained by non-linear least squares best-fitting to the equation Cleavage=$S/(1+[I]/[IC_{50}]$ where S is the amount of cleavage in the absence of inhibitor and I is the inhibitor concentration.

Table 1 summarizes the results of these assays and shows the $IC_{50}$ in µM for Compounds 1 through 14 as tested against the bimane derivatives of the acyl glucosaminyl inositol amidases of *M. tuberculosis* and *M. smegmatis*. Since there was little difference between inhibitory activity against the amidases of *M. tuberculosis* and *M. smegmatis* in the compounds tested against both enzymes, Compounds 10, 11, 13 and 14 were tested only against the *M. smegmatis* enzyme. As there is 80% amino acid sequence identity in the sequences of the two amidases, the inhibitory activity of Compounds 10, 11, 13 and 14 against the *M. tuberculosis* amidase is expected to closely mirror that against the *M. smegmatis* amidase.

EXAMPLE 3

To further elucidate the structural components of inhibitors of acyl glucosaminyl inositol amidase, such as S-conjugate amidase as described herein, three additional compounds were tested in the assay to screen for inhibition of the amidase activity as described in Examples 1 and 2 above using 50 µM MSmB as substrate, The first compound (C2385-2-2) referred to herein as C2385-2-2, is a dibromophenol derivative having a structural element in common with Compound 4, but with a basic site much nearer the phenolic ring than that in Compound 4. The results of the amidase inhibition assay showed that C23852-2 was ineffective as an amidase inhibitor, having an $IC_{50}$ of greater than 1 mM (FIG. 6).

By contrast, Oceanapiside, referred to herein as Compound 7, and the 3-alkylpyridinium macrocycles), referred to collectively herein as Compound 9 have substantially different structures with $IC_{50}$s, respectively of 5 µM and about 50 ng/ml.

This structural comparison illustrates that a common structural feature of Compounds 7, 8 and 9 is the presence of two sites that are positively charged, the two amines of oceanapiside being protonated at physiologic pH, linked by an intervening long hydrophobic chain. (See FIG. 6).

While the invention has been described in detail with reference to certain preferred embodiments thereof, it will be understood that modifications and variations are within the spirit and scope of that which is described and claimed.

That which is claimed is:
1. A compound having Structure I:

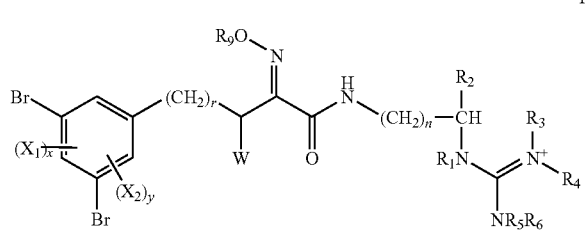

I wherein each of x and y independently has the value of 0 or 1, and each of $X_1$ and $X_2$ is —$O(CH_2)_mQ$, wherein m=1-4 and wherein Q is selected from the group consisting of —$NH_2$, —$NH(CH_2)_sCH_3$, —$N[(CH_2)_sCH_3]_2$, —$N^+[(CH_2)_sCH_3]_3$, and —$(CH_2)_sNH_2$, wherein s=0-3, n=1-6, and r=0-4;

W is selected from the group consisting of —H and —OH;

wherein each of $R_1$, $R_2$, $R_3$, $R_4$, $R_5$, and $R_6$ is independently selected from the group consisting of —H, —$CH_3$, and —$(CH_2)_pCH_3$, wherein p=0-3, $R_4$ is optionally present and —$CHR_2$ and $R_3$ can join to become —C=$CR_7$, forming an imidazole ring, and then $R_7$ is selected from the group consisting of: H,

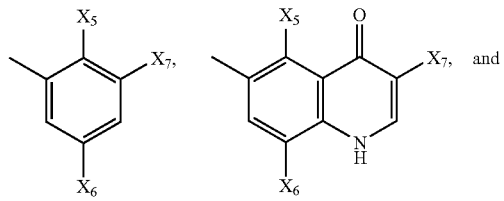

and

-continued

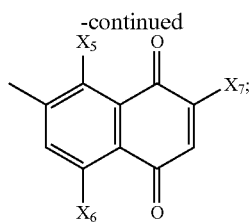

wherein each of $X_5$, $X_6$, and $X_7$ is independently selected from the group consisting of —H, —F, —Cl, —Br, —I, —OH, —OCH$_3$, —NH$_2$, —CONH$_2$ and —O(CH$_2$)$_m$Q, wherein m=1-4 and wherein Q is selected from the group consisting of —NH$_2$, —NH(CH$_2$)$_s$CH$_3$, —N[(CH$_2$)$_s$CH$_3$]$_2$, and —N$^+$[(CH$_2$)$_s$CH$_3$]$_3$, wherein s=0-3, n=1-6, and r=0-4; and wherein $R_9$ is selected from the group consisting of —H, CH$_3$, and (CH$_2$)$_s$CH$_3$, wherein s=0-3, and pharmaceutically suitable salts thereof.

2. The compound of claim 1, having Structure I, wherein m=3, Q is —NH$_2$, x=0, y=1, and n=1 or 2.

3. The compound of claim 1 having the chemical structure:

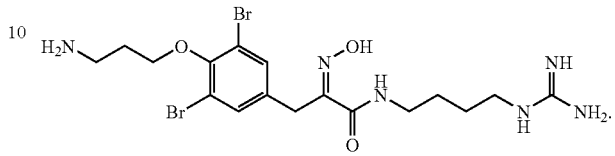

* * * * *

UNITED STATES PATENT AND TRADEMARK OFFICE
CERTIFICATE OF CORRECTION

PATENT NO.        : 7,642,280 B2                                                Page 1 of 1
APPLICATION NO.   : 10/474138
DATED             : January 5, 2010
INVENTOR(S)       : Fahey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 849 days.

Signed and Sealed this

Sixteenth Day of November, 2010

David J. Kappos
*Director of the United States Patent and Trademark Office*